United States Patent
Xu et al.

(10) Patent No.: US 7,826,124 B2
(45) Date of Patent: Nov. 2, 2010

(54) FLEXIBLE PANEL BASED ON ELECTROCHROMIC POLYMERS

(75) Inventors: Chunye Xu, Seattle, WA (US); Chao Ma, Seattle, WA (US); Minoru Taya, Mercer Island, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 106 days.

(21) Appl. No.: 12/244,285

(22) Filed: Oct. 2, 2008

(65) Prior Publication Data

US 2009/0052006 A1 Feb. 26, 2009

Related U.S. Application Data

(60) Continuation-in-part of application No. 11/932,834, filed on Oct. 31, 2007, now Pat. No. 7,547,658, which is a continuation of application No. 11/774,438, filed on Jul. 6, 2007, now Pat. No. 7,505,191, which is a division of application No. 11/070,392, filed on Mar. 1, 2005, now Pat. No. 7,256,923, which is a continuation-in-part of application No. 10/917,954, filed on Aug. 13, 2004, now Pat. No. 7,450,290, which is a continuation-in-part of application No. 10/755,433, filed on Jan. 12, 2004, now Pat. No. 7,002,722, which is a division of application No. 10/180,222, filed on Jun. 25, 2002, now Pat. No. 6,747,780.

(60) Provisional application No. 60/549,035, filed on Mar. 1, 2004, provisional application No. 60/495,310, filed on Aug. 14, 2003, provisional application No. 60/523,007, filed on Nov. 18, 2003, provisional application No. 60/300,675, filed on Jun. 25, 2001, provisional application No. 60/324,205, filed on Sep. 21, 2001, provisional application No. 60/364,418, filed on Mar. 14, 2002.

(51) Int. Cl.
*G02F 1/153* (2006.01)

(52) U.S. Cl. .................. 359/273; 359/275; 359/270; 359/272

(58) Field of Classification Search .............. 359/273, 359/275
See application file for complete search history.

(56) References Cited

U.S. PATENT DOCUMENTS 4,702,963 A  10/1987  Phillips et al. .............. 428/426

(Continued)

FOREIGN PATENT DOCUMENTS

JP         62265630       11/1987

*Primary Examiner*—Jessica T Stultz

(57) ABSTRACT

A flexible electrochromic (EC) panel that is usable for a display device or for other applications in which at least a region of the panel is selectively caused to change opacity. An exemplary EC panel includes an electrochromic working layer or electrode formed of a PProDOT-Me$_2$ polymer film that is deposited on an indium tin oxide (ITO)-coated polyethylene terephthalate (PET) flexible substrate. Similarly, a counter electrode is formed by depositing a vanadium oxide-titanium oxide ($V_2O_5$—$TiO_2$) composite film on another ITO PET coated flexible substrate. An ultraviolet light-cured film sealant is employed to seal the flexible panel and also serves as a spacer between the working and counter electrodes. The film sealant is patterned to define a volume for injecting an electrolyte solution through an inlet port provided in the film sealant. The inlet port is then closed. The EC panel can readily be flexed without damage.

22 Claims, 5 Drawing Sheets

U.S. PATENT DOCUMENTS

| | | | |
|---|---|---|---|
| 4,761,061 A | 8/1988 | Nishiyama et al. | 359/265 |
| 5,124,833 A | 6/1992 | Barton et al. | 359/269 |
| 5,598,293 A | 1/1997 | Green | 359/275 |
| 5,818,636 A * | 10/1998 | Leventis et al. | 359/273 |
| 6,033,592 A * | 3/2000 | Chandrasekhar | 252/62.2 |
| 6,157,479 A * | 12/2000 | Heuer et al. | 359/265 |
| 6,950,220 B2 | 9/2005 | Abramson et al. | 359/265 |
| 7,586,663 B1 * | 9/2009 | Radmard et al. | 359/265 |
| 2003/0156314 A1 * | 8/2003 | Shinozaki et al. | 359/273 |
| 2003/0174377 A1 * | 9/2003 | Reynolds et al. | 359/265 |
| 2005/0025980 A1 | 2/2005 | Agrawal et al. | 428/426 |
| 2007/0292606 A1 | 12/2007 | Demiryont et al. | 427/126.5 |
| 2008/0203910 A1 | 8/2008 | Reynolds | 313/506 |

* cited by examiner

FLEXIBLE PANEL BASED ON ELECTROCHROMIC POLYMERS

RELATED APPLICATIONS

This application is a continuation-in-part of copending patent application, Ser. No. 11/932,834, filed on Oct. 31, 2007, which is a continuation of Ser. No. 11/774,438, filed on Jul. 6, 2007, which itself is a divisional application based on prior patent application, Ser. No. 11/070,392, filed on Mar. 1, 2005, now issued as U.S. Pat. No. 7,256,923, which itself is based on a prior copending provisional application, Ser. No. 60/549,035, filed on Mar. 1, 2004, the benefits of the filing dates of which are hereby claimed under 35 U.S.C. §119(e) and 120. In addition, prior copending patent application, Ser. No. 11/070,392 is a continuation-in-part of a copending patent application, Ser. No. 10/917,954, filed on Aug. 13, 2004, which itself is based on two prior copending provisional applications, Ser. No. 60/495,310, filed on Aug. 14, 2003, and Ser. No. 60/523,007, filed on Nov. 18, 2003, the benefits of the filing dates of which are hereby claimed under 35 U.S.C. §119(e) and 120. Copending patent application Ser. No. 10/917,954 is also a continuation-in-part of prior patent application Ser. No. 10/755,433, filed Jan. 12, 2004, now issued as U.S. Pat. No. 7,002,722, which in turn is a divisional of prior application, Ser. No. 10/180,222, filed Jun. 25, 2002, now issued as U.S. Pat. No. 6,747,780, which is based on three provisional applications, Ser. No. 60/300,675, filed Jun. 25, 2001, Ser. No. 60/324,205, filed Sep. 21, 2001, and Ser. No. 60/364,418, filed Mar. 14, 2002, the benefit of the filing dates of which are hereby claimed under 35 U.S.C. §119(e) and 120.

BACKGROUND

Electrochromic (EC) materials are a subset of the family of chromogenic materials, which includes photochromic materials, and thermochromic materials. These materials change their tinting level or opacity when exposed to light photochromic), heat (thermochromic), or an electric potential (electrochromic). Chromogenic materials have attracted widespread interest in applications relating to the transmission of light.

An early application for chromogenic materials was in sunglasses or prescription eyeglasses that darken when exposed to the sun. Such photochromic materials were first developed by researchers at Corning Incorporated in the late 1960s. Since that time, it has been recognized that chromogenic materials could potentially be used to produce window glass that can vary the amount of light transmitted, although the use of such materials is clearly not limited to that prospective application. Another likely application will be in the production of display devices. Indeed, EC technology is already employed in the displays of digital watches.

Several different distinct types of EC materials are known. Three primary types are: inorganic thin films, organic polymer films, and organic solutions. For many applications, the use of a liquid EC material is inconvenient, and as a result, inorganic thin films and organic polymer films appear to have more industrial applications.

For inorganic thin film-based EC devices, the EC layer is typically tungsten oxide ($WO_3$). U.S. Pat. Nos. 5,598,293; 6,005,705; and 6,136,161 describe an inorganic thin film EC device based on a tungsten oxide EC layer. Other inorganic EC materials, such as molybdenum oxide, are also known. While many inorganic materials have been used as EC materials, difficulties in processing and a slow response time that is associated with many inorganic EC materials have created the need to develop different types of EC materials.

Conjugated, redox-active polymers represent one different type of EC material. These polymers (cathodic or anodic polymers) are inherently electrochromic and can be switched electrochemically (or chemically) between different color states. A family of redox-active copolymers are described in U.S. Pat. No. 5,883,220. Another family of nitrogen-based heterocyclic organic EC materials is described in U.S. Pat. No. 6,197,923. Research into still other types of organic film EC materials continues, in hopes of identifying or developing EC materials that will be useful in commercial applications such as EC windows. There still exists room for improvement and development of new types of EC organic polymer films, and methods of making EC organic polymer films.

The EC devices that have thus far been constructed employ relatively rigid substrates. Polymer films are readily deposited on glass, and it is typically employed for this purpose when fabricating EC devices. However, for certain applications, it would be preferable to produce an ECD that is entirely flexible. Since a flexible ECD that is actuated with an applied electrical potential must retain the spacing between the working and counter electrodes comprising the device, it is not trivial to construct such a device. A flexible ECD must be capable of retaining the seal that keeps an electrolyte between the two electrodes, even when the device is repeatedly flexed. The configuration must enable bending of the device without sustaining damage.

SUMMARY

As used herein the term flexible ECD clearly indicates an electrochromic display that is flexible and can be bent without being damaged. An initial effort was made to create such a display, and much of the following discussion is directed to the procedure for fabricating the device. However, it should be understood that in a broader sense, the present novel approach is intended to produce a flexible EC panel and is not limited specifically to the use of a flexible panel only as a display device. For example, instead of being used for a display, a flexible EC panel might be included in sunglasses. The lens portion of the glasses comprising the flexible EC panel would be more readily fabricated as a planar multilayer configuration, but when mounted in the frames, would have the capability of being readily bent or flexed to conform to a frame that is designed to curve around a user's eyes. Accordingly, it will be understood that discussion of a "flexible ECD" is not intended to be limited only to a display device, but instead, is intended to more broadly apply to a flexible EC panel.

More specifically, one aspect of this novel technology is directed to an exemplary method for producing a flexible electrochromic panel. The method includes the steps of depositing a working electrochromic film on a first flexible polymer substrate. The working electrochromic film is selected for its ability to repetitively change between at least a first state in which the working electrochromic film exhibits a first transmittance characteristic, and a second state in which the working electrochromic film exhibits a second, substantially different transmittance characteristic. The term substantially different should be understood to mean that the different transmittance characteristics can be differentiated by the naked eye. In an exemplary embodiment, in the first state the working electrochromic film is generally an opaque color, and in the second state the working electrochromic film is substantially transparent. The change between states occurs as a result of the working electrochromic film undergoing a redox process.

The specific use of the flexible electrochromic panel will generally determine how different the first and second transmittance characteristics will be. Furthermore, it should be recognized that the transmittance characteristics of some electrochromic polymers in the different states is a function of the applied voltage, such that one can vary the voltage applied to the EC polymer to selectively vary its transmittance (i.e., the EC polymer is oxidized or reduced, depending on the applied voltage, and different voltages can be applied to vary the degree of oxidation or reduction, resulting in changing the relative transmittance of the EC polymer).

Referring once again to the deposition of the ITO conductive layer on a first flexible polymer substrate; similarly, an ion storage film is deposited on a second flexible polymer substrate. The ion storage film chemically interacts with the working electrochromic film during the redox process. The first and the second flexible polymer substrates are selected for a characteristic flexibility that enables them to be readily bent in an arc. The first and the second flexible polymer substrates are then coupled together with a film sealant that is disposed between them. The film sealant serves as a spacer and defines a volume that is disposed between the working electrochromic film and the ion storage film. An electrolyte solution is injected into the volume defined by the film sealant. The flexible electrochromic panel is then sealed to exclude moisture and oxygen, and to maintain the electrolyte solution within the volume. The flexible electrochromic panel that is thus produced is capable of being bent in a substantial curve without experiencing damage.

The step of sealing the flexible electrochromic panel can include the step of curing the film sealant with ultraviolet light.

The film sealant can also define an inlet port in fluid communication with the volume. The step of injecting the electrolyte solution into the volume can then include the step of injecting the electrolyte solution through the inlet port. In this case, the step of sealing can include the step of sealing the inlet port with a sealant material after the electrolyte has been injected into the volume.

Another step of the method is providing terminals on the flexible electrochromic panel to enable a voltage to be applied to the working electrochromic film and to the ion storage film for selectively changing the working electrochromic film between the first state and the second state.

In at least one exemplary embodiment, the method further includes the step of coating the first and the second flexible polymer substrates with an indium tin oxide (ITO) coating before depositing the working electrochromic film and the ion storage film on the flexible substrates. While ITO represents an exemplary conductive coating, it should be recognized that other conductive coatings can be employed. In many embodiments generally transparent coatings are preferred, however, it should be understood that in some embodiments a tinted coating may be acceptable, or even preferred.

An exemplary embodiment employs a polyethylene terephthalate (PET) material for the first and the second flexible polymer substrates and a vanadium oxide-titanium oxide composite for the ion storage film. While PET represents an exemplary flexible polymer substrate, it should be recognized that other flexible polymer substrates can be employed. The method can then include the step of baking the ion storage film deposited on the second flexible polymer substrate at a sufficiently elevated temperature so as to evaporate a liquid from the vanadium oxide-titanium oxide composite that is deposited on the second flexible polymer substrate, while avoiding thermal damage to the second flexible polymer substrate. At least one exemplary embodiment uses dimethyl substituted poly(3,4-propylenedioxythiophene) for the working electrochromic film, although it is contemplated that many other types of polymers might instead be used for this purpose. Dimethyl substituted poly(3,4-propylenedioxythiophene) is also known as poly(3,4-(2,2-dimethylpropylene-dioxy)thiophene) and poly[3,3-dimethyl-3,4-dihydro-2H-thieno[3,4-b][1,4]dioxepine]; and is referred to in abbreviated format as PProDOT-Me$_2$.

Another aspect of the novel technology is directed to a flexible electrochromic panel that is configured generally as discussed above in regard to the method for making such a device.

This application specifically incorporates by reference the disclosures and drawings of each patent application and issued patent identified above as a related application.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figures 8A, 8B:
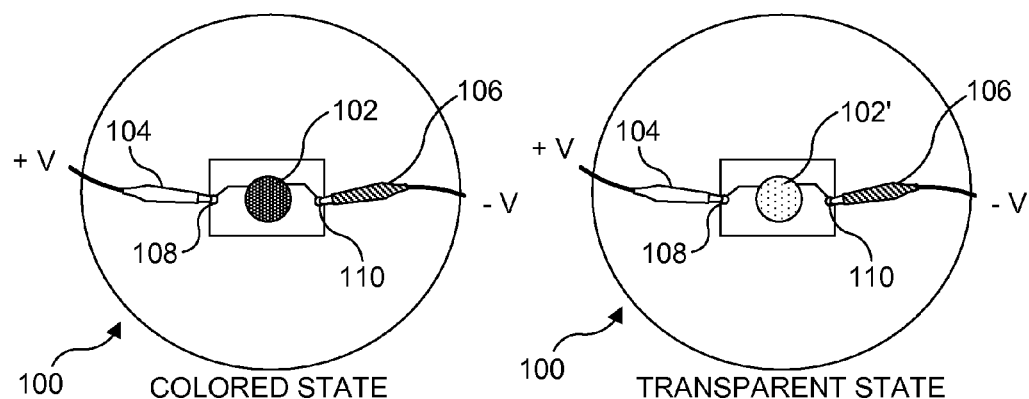
Figures 9A, 9B:
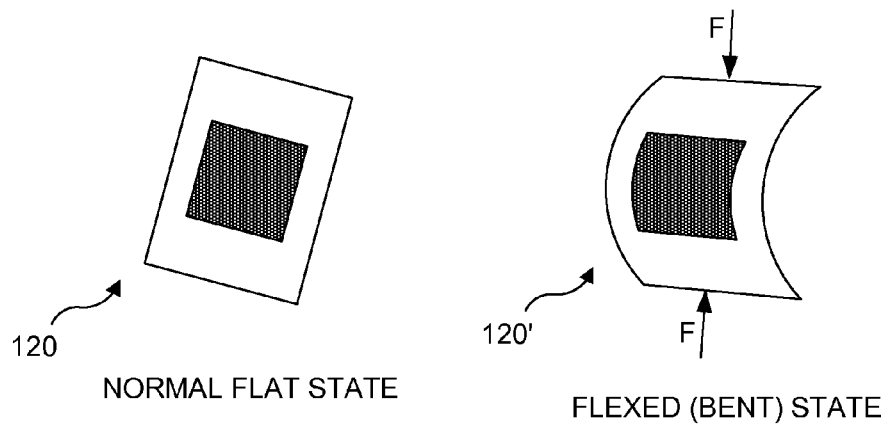
Figure 10:
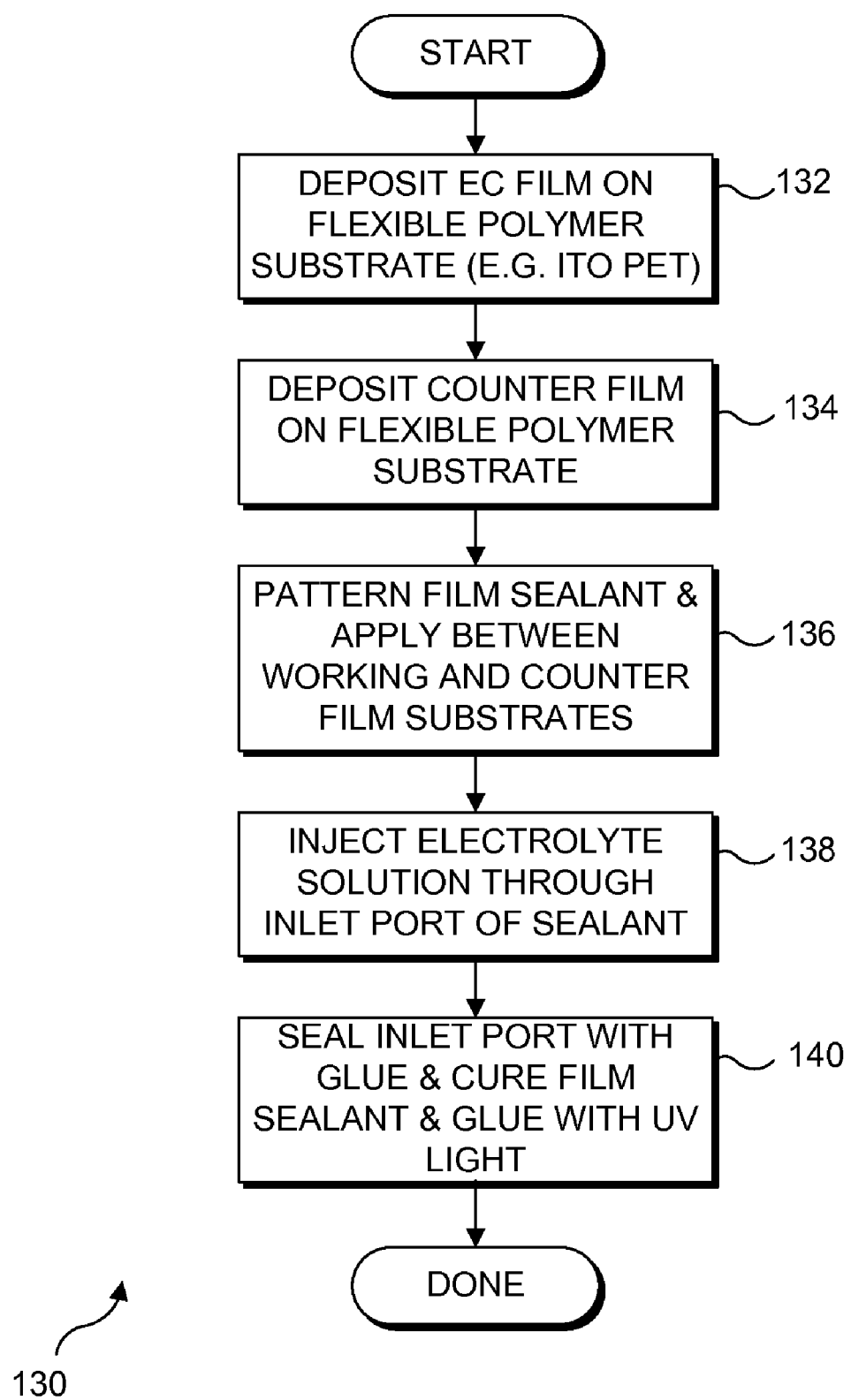

FIGS. 8A and 8B respectively illustrate an exemplary flexible ECD in its transparent state and its colored (opaque) state as the appropriate potential is applied to switch to each of these states by leads attached to terminals on the device;

FIGS. 9A and 9B respectively illustrate an exemplary flexible ECD in its normal flat state, and in its flexed or bent state that is achieved when opposed forces are applied to opposite ends of the device; and FIG. 10 is a flowchart illustrating steps that are carried out to fabricate the exemplary flexible ECD.

DESCRIPTION

Figures and Disclosed Embodiments Are Not Limiting

One or more exemplary embodiments are illustrated in referenced Figures of the drawings. It is intended that each embodiment and the Figures disclosed herein are to be considered illustrative rather than restrictive. No limitation on the scope of the technology and of the claims that follow is to be imputed to the examples shown in the drawings and discussed herein.

Several new kinds of electrochromic polymer materials have been developed that are blue, red, or green in color and which can be employed to produce a full color display. An initial exemplary embodiment of the present novel approach employs a cathodic EC polymer material, poly[3,3-dimethyl-3,4-dihydra2H-thieno[3,4-b][1,4]dioxepine] (PProDOT-Me$_2$), as a working material on which to fabricate a flexible electrochromic display (ECD) that can be controllably changed from a transparent state to a blue colored (opaque) state by applying an appropriate potential across the counter and working electrodes of the device. The PProDOT-Me$_2$ EC film exhibits a high transmittance contrast ratio (having 0% transmittance in its colored state) between a blue color and a transparent state, operates at low potentials, has high conductivity, and exhibits excellent thermal stability. It will be understood that other EC films having different colors can alternatively be employed in the flexible ECD, and it is contemplated that a plurality of different colors can be selectively provided by fabricating a flexible ECD with a plurality of different EC films, to produce a multicolor display or panel. The flexibility of this ECD device makes it useful in many applications in which a rigid ECD fabricated using glass substrates would be unacceptable and readily broken, if the display or panel were flexed or bent while in use or during construction of the product that includes the EC device.

Figure 1:
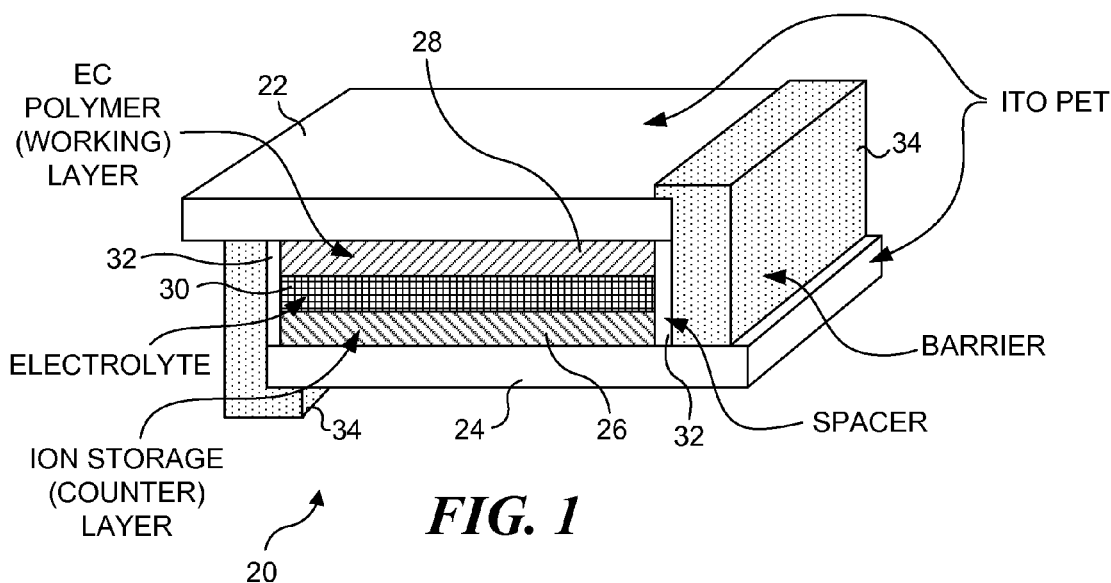
FIG. 1 is a schematic diagram illustrating the layers of an exemplary flexible ECD configured in accord with the present novel approach.

An exemplary flexible ECD 20 comprises a multilayer electrochromic polymer configuration, as illustrated in FIG. 1. An electrochromic working layer 28, i.e., the PProDOT-Me$_2$ polymer film, is deposited on an indium tin oxide (ITO)-coated polyethylene terephthalate (PET) substrate 22, which is relatively flexible, in contrast to the rigid glass or the non-flexible polymer substrates used in prior electrochromic devices. In making this exemplary embodiment, the PProDOT-Me$_2$ polymer film was deposited from a 0.01 M monomer in a 0.1 M LiClO$_4$/Acetonitrile (ACN) solution on ITO coated PET substrate 22 (obtained from Sheldahl, Inc. of Minnesota), which has a surface resistance of about 20 Ω.

An oxidative electrochemical polymerization method was used to deposit polymer films onto the ITO PET substrate in this exemplary embodiment. The monomer is oxidized and forms a radical cation, which undergoes a further coupling reaction with other monomers or radical cations, forming insoluble polymer chains on the electrode surface of the ITO PET substrate. The applied potential during the deposition is 1.5-2.5 V, and the deposition time is from about 1 s to about 15 s. Due to the relatively low quality and conductivity of the ITO coating on the PET substrate, a copper tape can be applied to minimize the potential drop through the substrate surface.

A counter layer 26 of the flexible ECD is a vanadium oxide-titanium oxide (V$_2$O$_5$—TiO$_2$) composite film, which is also deposited on an ITO PET substrate 24 that is substantially identical to ITO coated substrate 22. To deposit the V$_2$O$_5$—TiO$_2$ composite film onto the ITO PET substrate, an applied potential controlled to be about 3.5 V was used, resulting in a deposition time of about 10 s to about 20 s. However, excess liquid needs to be evaporated from the deposited V$_2$O$_5$—TiO$_2$ composite film, which can be accomplished by baking the assembly in an oven at over 100° C. Since the PET plastic comprising this substrate can experience a damaging deformation during heating at such an elevated temperature, it is necessary to carefully control the baking time and temperature. After being coated with the V$_2$O$_5$—TiO$_2$ composite film, the PET substrate is placed on a flat glass substrate support and heated to about 104° C. for 4 h.

This exemplary embodiment also includes a transparent electrolyte layer 30, which is a good conductor for small ions, such as ClO$_4^-$ and Li$^+$, and an insulator for electrons. The transparent liquid electrolyte layer is sandwiched between the working and counter layers. This transparent liquid electrolyte layer serves as an ion transport layer, and ions move quickly inside the transparent electrolyte layer during switching of the display device between states. Note that a gel or solid electrolyte can also be used, although empirical studies have suggested that liquid electrolytes offer enhanced performance. The V$_2$O$_5$—TiO$_2$ composite film serves as an ion storage layer (i.e., an ion attracting layer) and works with the PProDOT-Me$_2$ film—each forming one part of a pair. When the EC film is reduced with an applied potential and changes color to blue (attracting positively charged lithium (Li) ions), the V$_2$O$_5$—TiO$_2$ film simultaneously attracts negatively charged perchlorate (ClO$_4$) ions. When the EC film is oxidized with an opposite potential and changes to its transparent state (attracting negatively charged perchlorate (ClO$_4$) ions), the V$_2$O$_5$—TiO$_2$ film attracts positively charged Li$^+$ ions. While switching between these two states, the V$_2$O$_5$—TiO$_2$ film maintains a light green color. The relatively light tint provided by the V$_2$O$_5$—TiO$_2$ film is acceptable for most applications. If a more optically transparent counter layer is desired, (i.e., a counter layer without the green tint), other counter layers, such as patterned gold or graphite layers, can also be employed.

Figure 2:
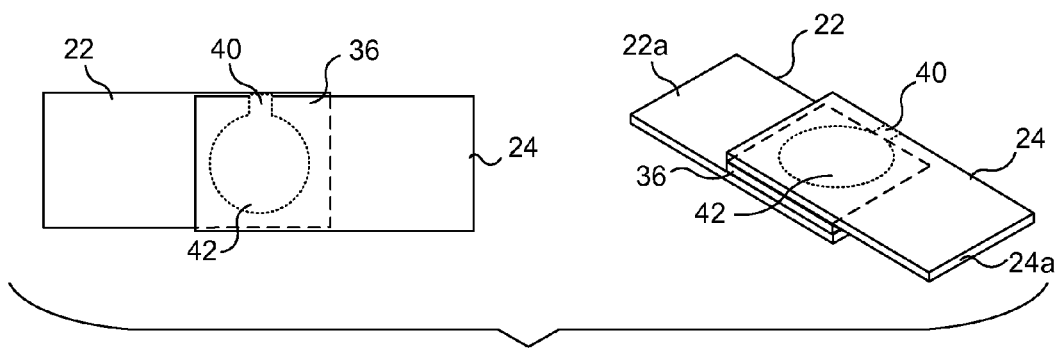
FIG. 2 illustrates a schematic plan view and an isometric view of the exemplary flexible ECD that is being fabricated, showing the patterned inlet port of a film sealant layer that is adherently disposed between the counter layer and the working layer.

For this exemplary embodiment of the flexible substrate device, an ultraviolet (UV) light cured film sealant 36 (FIG. 2) was adopted to seal the flexible ECD. This cured film sealant serves as spacer 32 (see FIG. 1) that is sized to maintain about a 30 μm gap between the working and counter electrodes, while also serving as a barrier (in addition to barrier 34) to prevent moisture and oxygen absorption by the display device. The cured film sealant thus maintains the separation between the two electrodes, while sealing the flexible ECD, and is patterned to provide an inlet port 40 into a relatively thin volume 42 for holding liquid electrolyte (FIG. 1), as shown in FIG. 2. The liquid transparent electrolyte solution is injected through the inlet port of the film sealant, and inlet port 40 is then sealed with a glue or other suitable adhesive/sealant. It should be recognized that the concepts disclosed herein encompass embodiments in which the cured film sealant also functions as barrier 34 (such that separate barrier and spacer elements are not required, with the cured film sealant simultaneously implementing both elements).

Referring to FIG. 2, note that while substrate 22 and 24 overlap in a center portion of the device (i.e., proximate thin volume 42), a right edge 24a (relative to the drawing figure) of substrate 24 extends beyond the center portion, and a left edge 22a (relative to the drawing figure) of substrate 22 extends beyond the center portion. Significantly, the substrates do not overlap at these edge portions. The specific dimensions of the edge portions are not critical, but these edge portions do provide a functional role, in that electrical connections can be made relatively easily at these edge portions. FIGS. 8A and 8B schematically illustrate such connections. Thus, the edges act as terminals for electrical connections.

Figure 3:
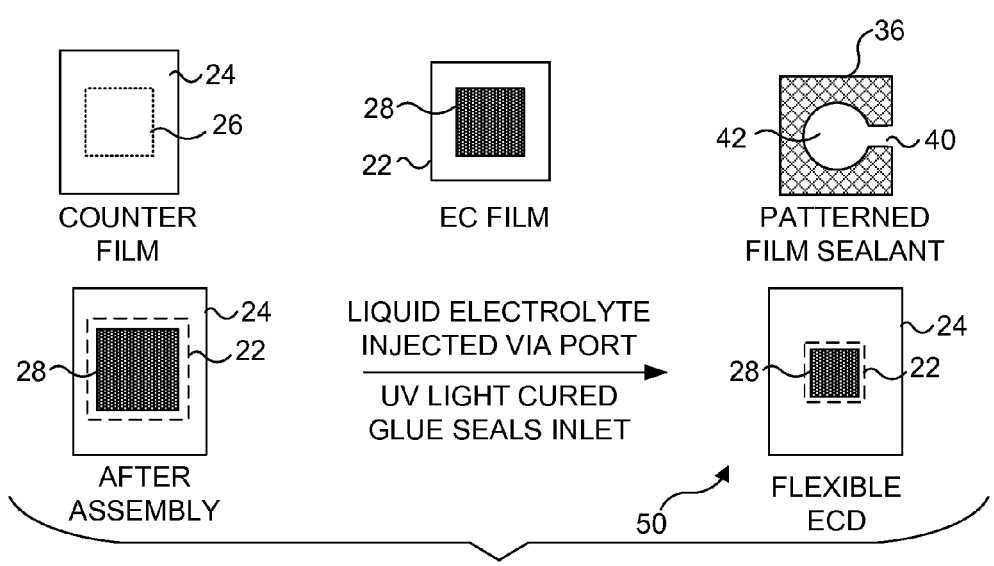
FIG. 3 illustrates exemplary fabrication steps and components used for making a flexible ECD in accord with the present novel approach.

The components that are assembled to produce a flexible ECD 50 are shown in FIG. 3. The steps used for fabricating flexible ECD 50 are illustrated in FIG. 10, and the following discussion is directed to both FIGS. 3 and 10. In a flowchart 130, in steps 132 and 134, working layer 28 comprising the EC film, and counter layer 26 comprising the $V_2O_5$—$TiO_2$ composite film are respectively deposited on ITO PET substrates 22 and 24. Film sealant 36 is patterned and applied between the working and counter substrates in a step 136. In a step 138, the liquid electrolyte solution is then injected through inlet port 40 provided in the patterned film sealant. After this electrolyte injection is completed, in a step 140, the open inlet port is sealed using a UV curable glue or other suitable adhesive or sealant, and the entire device is then irradiated with UV light for about 10 minutes, which causes the sealant to fully bond between the two substrate layers and to become impermeable to moisture and oxygen. Before the UV light is used for curing the sealant, the flexible ECD, barriers 34 (see FIG. 1) can be provided to more fully seal the ends of the layers comprising the flexible ECD, but are not shown in FIG. 3, and this aspect is not included as a step shown in FIG. 10.

Figure 4:
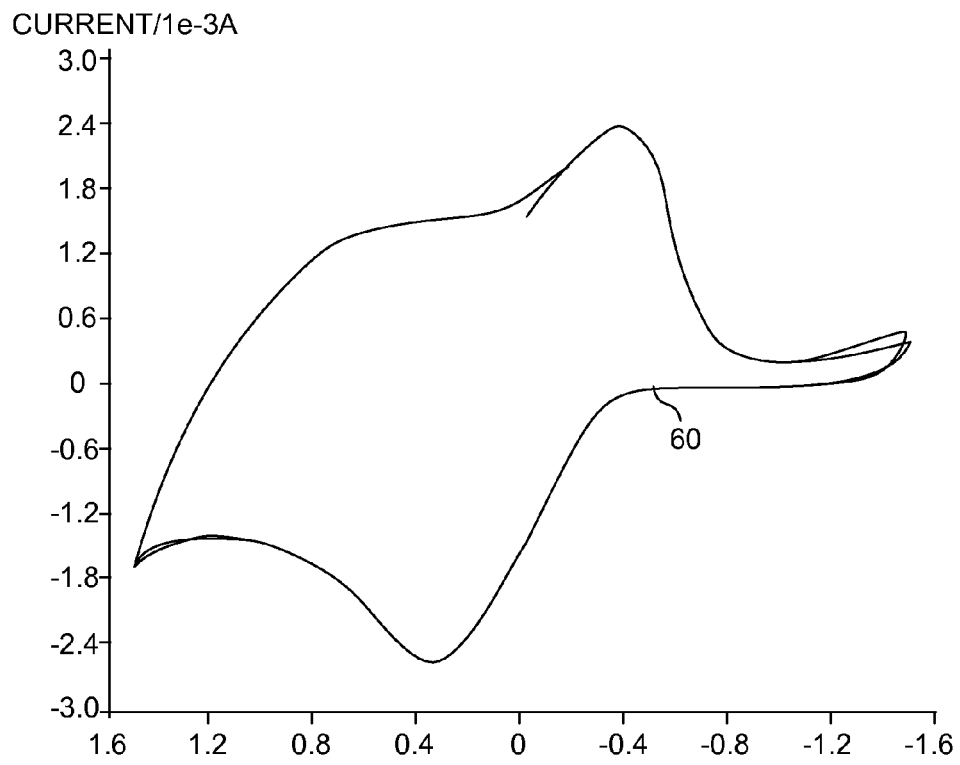
FIG. 4 is a graph showing an exemplary cyclic voltammetry (CV) curve of the electrochromic (EC) film on the flexible substrate for a potential range from about −1.5 V to about +1.5 V.
Figure 5:
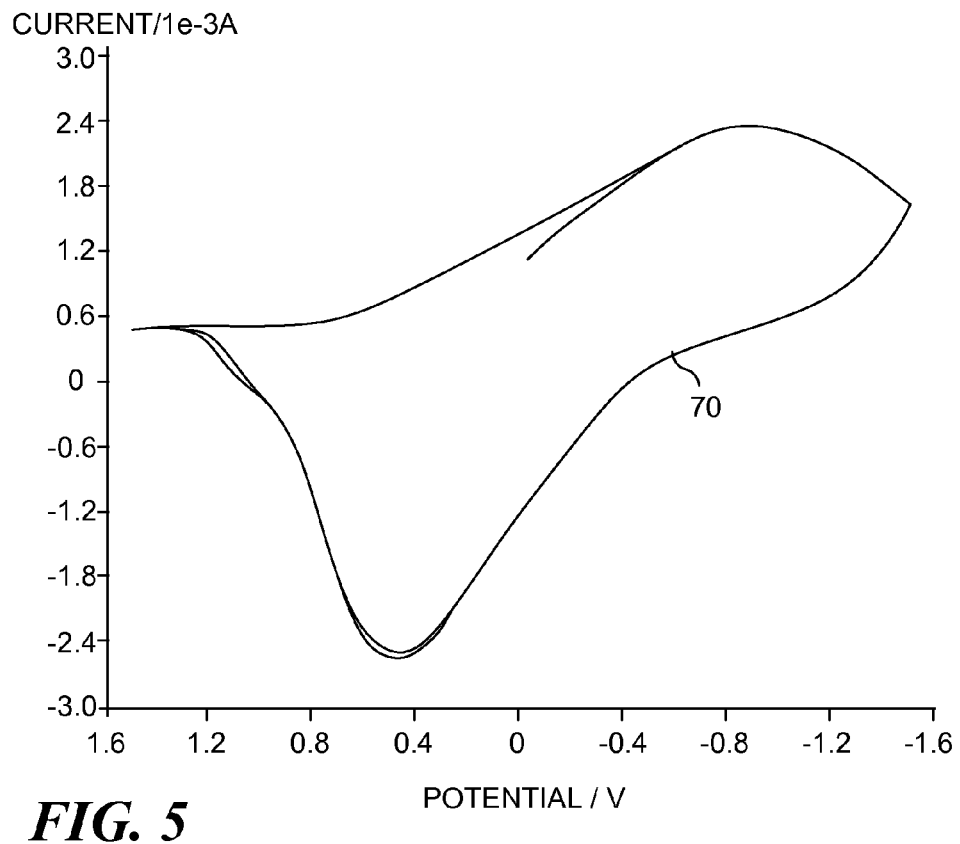
FIG. 5 is a graph showing an exemplary CV curve of the counter film, which requires a potential of about 0.8 V to about 1.0 V.

FIG. 4 illustrates an exemplary cyclic voltammetry (CV) curve 60 of the EC film for the flexible substrate, which ranges from about −1.5 V to about +1.5 V in potential. Two peaks (positive and negative), which indicate the reduction and oxidation of the EC polymer, can be observed around ±0.4 V. Although the redox potential of the EC polymer is around ±0.4 V, a potential of about ±1.2 V is actually used to operate this flexible ECD, because the redox of the $V_2O_5$—$TiO_2$ counter film requires a higher potential, i.e., approximately 0.8 V-1.0 V, as shown by a CV curve 70 in FIG. 5.

Figure 6:
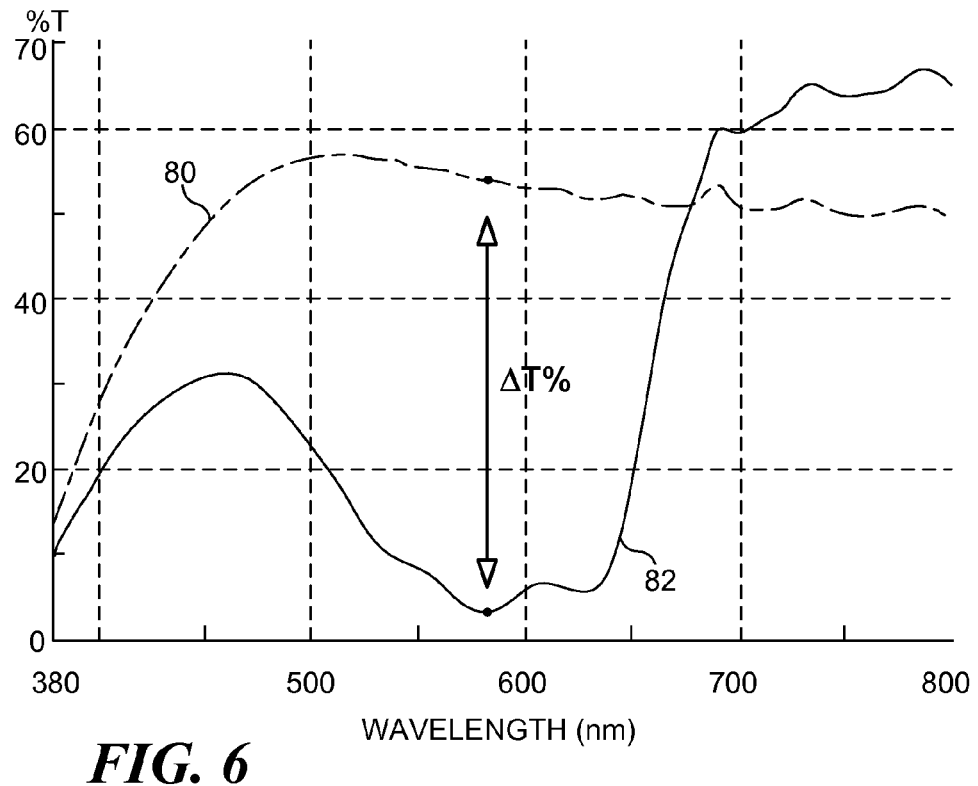
FIG. 6 is a graph illustrating the typical transmittance as a function of wavelength for both the transparent and opaque states, for a plurality of flexible ECDs configured according to the present novel approach.
Figure 7A:
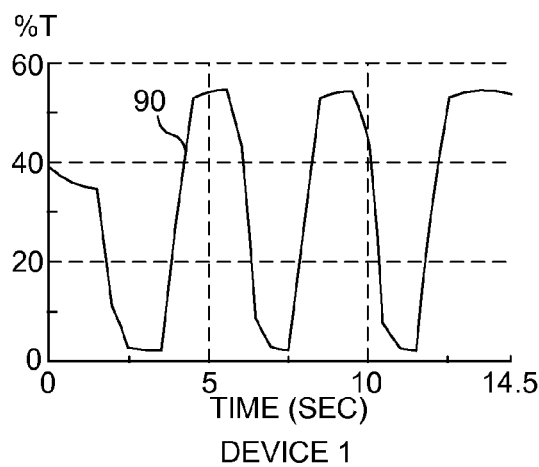
FIGS. 7A-7D are graphs illustrating the response time for switching states as the applied potential is alternately stepped between −1.2 V and +1.2 V for each of four different flexible ECDs configured according to the present novel approach.
Figure 7B:
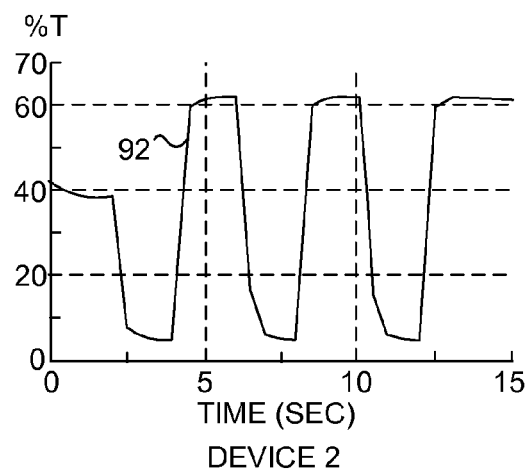
Figure 7C:
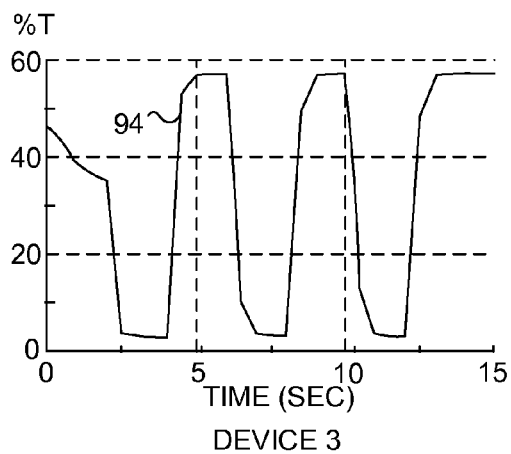
Figure 7D:
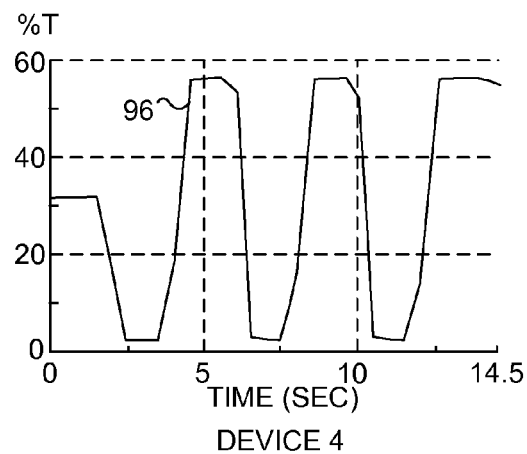

The measurement of light transmittance (i.e., T %) by the device was carried out using a UV-vis-NIR spectrometer. Several flexible devices were fabricated and a typical (average) T % for visible light wavelengths was measured, yielding the results shown in FIG. 6. A flat line curve 80 at the top of the graph in this Figure represents T % in the transparent state of the devices, and indicates that the device provides high transmittance in the visible light range. A "U" shaped curve 82 at the bottom of the graph is the T % in the opaque state and has a minimum transmittance in the range of 550 nm-600 nm, which is the most sensitive portion of the visible light spectrum, to human eyes. Here, the contrast ratio of light transmittance at a certain wavelength (ΔT %) is defined as the difference between T % for the transparent and the opaque states at that wavelength. The highest contrast ratio, $\Delta T\%_{max}$, for these exemplary display devices appears at a wavelength of about 580 nm, as indicated by the double arrowhead line in FIG. 6.

FIGS. 7A-7D illustrate the measured results of reversing the potential applied to four devices, in regard to the cyclic light transmittance. This technique is used to test the response time and repeatability of the display devices. In this test, the potential was stepped between −1.2 V and +1.2 V, with a delay time of about 2 seconds between each stepped change in the potential polarity.

The light transmittance was measured at 580 nm wavelength. For different devices, different $T\%_{max}$, $T\%_n$, and ΔT % were measured. For a device 1, a curve 90 indicates that the range was from 54% for the transparent state, to 2% for the opaque state, with ΔT %=52%. For device 2, a curve 92 indicates that the range was from 62% to 5%, with ΔT %=57%. For device 3, a curve 94 indicates that the range was from 57% to 3%, with ΔT %=54%. And, for device 4, a curve 96 indicates that the range was from 56% to 3%, with ΔT %=53. The range of these parameters is controlled by the thickness of the EC polymer film, i.e., the thicker the EC polymer film, the darker will be the film; and conversely, the thinner the EC polymer film, the lighter will be the film. The thickness of the EC polymer film can be controlled during film deposition by adjusting parameters such as deposition potential and charging time. The response time of the flexible devices is relatively fast, since they can be switched from a completely transparent state to a completely opaque state (and vice versa) in about 1 second.

The exemplary flexible ECDs that were produced as described above exhibited good stability over 40,000 cycles of switching between states. A test setup 100 for the flexible ECDs is illustrated in FIGS. 8A and 8B. In this test setup, the flexible ECD was changed from a colored or opaque state 102 as shown in FIG. 8A to a transparent state 102', as shown in FIG. 8B, by applying the appropriate potential through leads 104 and 106, which are clipped to terminals 108 and 110, respectively. During these tests, the light transmittance for the colored state displayed almost no change. The light transmittance of the transparent state decreased slightly during the first 5,000 cycles, but became stable after that. At the beginning of this test, the light transmittance was about 55.2%±2.4%, and after 40,000 cycles, it had decreased to about 52.1%±2.6%.

FIGS. 9A and 9B respectively illustrate a device made in accord with the novel approach described above in a normal flat state 120, and in a flexed or bent state 120', which is achieved when a force F is applied to opposite edges of the flexible ECD causing the edges to move toward each other and the center of the flexible ECD to bend outwardly. The capability of the flexible ECD to bend without being damaged enables it to be used in any application where such bending of the device may occur. In contrast, prior art rigid ECDs would be damaged if an attempt were made to flex them in this manner.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for producing a flexible electrochromic panel, comprising the steps of:
   (a) depositing a working electrochromic polymer film layer comprising insoluble polymer chains of an organic material exhibiting electrochromic properties on a first flexible polymer substrate using electrochemical polymerization, the working electrochromic polymer film layer being selected for its ability to repetitively change between at least:
   (i) a first state in which the working electrochromic polymer film layer exhibits a first transmittance characteristic; and
   (ii) a second state in which the working electrochromic polymer film layer exhibits a second transmittance characteristic, where the first and second transmittance characteristics are substantially different, as a result of the working electrochromic film undergoing a redox process;
(b) depositing an ion storage film on a second flexible polymer substrate, the ion storage film chemically interacting with the working electrochromic polymer film layer during the redox process, wherein the first and the second flexible polymer substrates are selected for a characteristic flexibility that enables them to be readily bent in an arc;
(c) coupling the first and the second flexible polymer substrates together with a film sealant such that the film sealant is disposed between the working electrochromic polymer film layer deposited on the first flexible polymer substrate and the ion storage film deposited on the second flexible polymer substrate, the film sealant being configured to space the working electrochromic polymer film layer apart from the ion storage film and defining a patterned opening and an inlet port in fluid communication with the opening, wherein the opening is disposed between the working electrochromic polymer film layer and the ion storage film, and wherein the opening has a larger volume than the inlet port;
(d) introducing an electrolyte into the opening defined by the film sealant; and
(e) sealing the flexible electrochromic panel to exclude moisture and oxygen, and to maintain the electrolyte within the opening, the flexible electrochromic panel being capable of being bent in a substantial curve without experiencing damage.

2. The method of claim 1, wherein the step of introducing the electrolyte comprises the step of introducing a liquid electrolyte.

3. The method of claim 1, wherein the step of sealing the flexible electrochromic panel comprises the step of curing the film sealant with ultraviolet light.

4. The method of claim 1, wherein the step of injecting the electrolyte solution into the opening comprises the step of introducing the electrolyte through the inlet port.

5. The method of claim 4, wherein the step of sealing includes the step of sealing the inlet port with a sealant material after the electrolyte has been introduced into the opening.

6. The method of claim 1, further comprising the step of providing terminals on the flexible electrochromic panel to enable a voltage to be applied to the working electrochromic polymer film layer and to the ion storage film for selectively changing the working electrochromic polymer film layer between the first state and the second state.

7. The method of claim 1, further comprising the step of coating the first and the second flexible polymer substrates with an indium tin oxide (ITO) coating before the steps of depositing the working electrochromic polymer film layer and the ion storage film.

8. The method of claim 1, further comprising the step of using a polyethylene terephthalate (PET) material for the first and the second flexible polymer substrates.

9. The method of claim 1, further comprising the step of using a vanadium oxide-titanium oxide composite for the ion storage film.

10. The method of claim 9, further comprising the step of baking the ion storage film deposited on the second flexible polymer substrate at a sufficiently elevated temperature so as to evaporate a liquid from the vanadium oxide-titanium oxide composite that is deposited on the second flexible polymer substrate, while avoiding thermal damage to the second flexible polymer substrate.

11. The method of claim 1, further comprising the step of using a PProDOT-$Me_2$ polymer for the working electrochromic polymer film.

12. A flexible electrochromic panel, comprising:
(a) a first flexible polymer substrate on which a working electrochromic polymer film layer comprising insoluble polymer chains of an organic material exhibiting electrochromic properties is electrochemically polymerized, the working electrochromic polymer film layer being selected for its ability to repetitively change between at least:
  (i) a first state in which the working electrochromic polymer film layer exhibits a first transmittance characteristic; and
  (ii) a second state in which the working electrochromic polymer film layer exhibits a second transmittance characteristic, where the first and second transmittance characteristics are substantially different, as a result of the working electrochromic film undergoing a redox process;
(b) a second flexible polymer substrate on which is deposited an ion storage film, the ion storage film chemically interacting with the working electrochromic polymer film layer during the redox process, wherein the first and the second flexible polymer substrates are characterized by being relatively flexible and readily bent in an arc;
(c) a film sealant that couples the first and the second flexible polymer substrates together, the film sealant being configured to space the working electrochromic polymer film layer and the ion storage film apart from one another, the film sealant including a patterned opening and an inlet port in fluid communication with the opening, wherein the opening is disposed between the working electrochromic polymer film layer and the ion storage film, and wherein the opening has a larger volume than the inlet port; and
(d) an electrolyte disposed within the opening defined by the film sealant, the electrolyte providing and conducting ions between the working electrochromic polymer film layer and the ion storage film during the redox process, to enable the working electrochromic polymer film layer to change between the first and the second states.

13. The flexible electrochromic panel of claim 12, wherein the film sealant is formed of a material that is cured by exposure to an ultraviolet light, to adhesively join the first flexible polymer substrate to the second flexible polymer substrate.

14. The flexible electrochromic panel of claim 12, wherein the film sealant further defines the inlet port such that the inlet port provides a fluid path into the opening for introducing the electrolyte into the opening.

15. The flexible electrochromic panel of claim 14, further comprising a sealant material introduced into the inlet port to seal the inlet port after the electrolyte has been introduced into the opening.

16. The flexible electrochromic panel of claim 12, further comprising terminals that are electrically coupled to the working electrochromic film and to the ion storage film, for selectively applying a potential to cause the working electrochromic polymer film layer to change between the first state and the second state.

17. The flexible electrochromic panel of claim 12, wherein the first and the second flexible polymer substrates each include an indium tin oxide (ITO) coating respectively underlying deposits of the working electrochromic film and the ion storage film.

18. The flexible electrochromic panel of claim 12, wherein the first and the second flexible polymer substrates are each formed of a polyethylene terephthalate (PET) material.

19. The flexible electrochromic panel of claim 12, wherein the ion storage film comprises a vanadium oxide-titanium oxide composite.

20. The flexible electrochromic panel of claim 12, wherein the working electrochromic polymer film layer comprises a PProDOT-Me$_2$ polymer.

21. The flexible electrochromic panel of claim 12, wherein the electrolyte comprises a liquid electrolyte.

22. The flexible electrochromic panel of claim 12, further comprising a barrier disposed around one or more edges to seal the flexible electrochromic panel, preventing entry of liquid and oxygen from a surrounding environment.

* * * * *